United States Patent [19]

Patchett

[11] Patent Number: 4,555,503

[45] Date of Patent: Nov. 26, 1985

[54] N²-(SUBSTITUTED)CARBOXYMETHYL-N⁶-(SUBSTITUTED)-LYSYL-AND α-(ε-AMINOALKYL)GLYCYL AMINO ACID ANTIHYPERTENSIVE AGENTS

[75] Inventor: Arthur A. Patchett, Westfield; Mu T. Wu, Clark, both of N.J.

[73] Assignee: Merck & Co., Inc., Rahway, N.J.

[21] Appl. No.: 466,622

[22] Filed: Feb. 18, 1983

Related U.S. Application Data

[63] Continuation-in-part of Ser. No. 374,834, May 5, 1982, abandoned.

[51] Int. Cl.⁴ .................... A61K 37/00; C07C 103/52
[52] U.S. Cl. ................. 514/19; 260/112.5 R
[58] Field of Search ............... 260/112.5 R; 424/177; 514/19

[56] References Cited

U.S. PATENT DOCUMENTS 4,113,715  9/1978  Ondetti et al. .............. 260/112.5 R
4,129,571  12/1978  Ondetti et al. .............. 260/112.5 R
4,154,960  5/1979  Ondetti et al. .............. 260/112.5 R

FOREIGN PATENT DOCUMENTS 0012401  6/1980  European Pat. Off. ..... 260/112.5 R
0050800  5/1983  European Pat. Off. ..... 260/112.5 R
2095682  10/1982  United Kingdom ........ 260/112.5 R Primary Examiner—Delbert R. Phillips Attorney, Agent, or Firm—Salvatore C. Mitri; Michael C. Sudol

[57] ABSTRACT

Compounds of the formula:

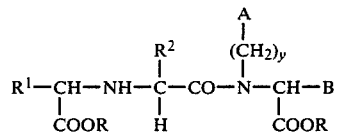

wherein R² is

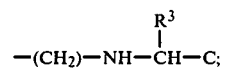

wherein k is 2 to 5; R³ is hydrogen; loweralkyl and substituted loweralkyl where the substituents are carboxy, hydroxy, and amino; or aralkyl, substituted aralkyl, heteroaralkyl, and substituted heteroaralkyl where the aryl and heteroaryl substituents are carboxy, hydroxy, and amino; and C is COOR; CONH₂; or CH₂OH; and a pharmaceutically acceptable salt thereof; are inhibitors of angiotensin I converting enzyme useful as antihypertensive agents.

22 Claims, No Drawings

N²-(SUBSTITUTED)CARBOXYMETHYL-N⁶-(SUBSTITUTED)-LYSYL-AND α-(ε-AMINOALKYL)GLYCYL AMINO ACID ANTIHYPERTENSIVE AGENTS

BACKGROUND OF THE INVENTION

1. Field of the Invention

This application is a continuation-in-part of application Ser. No. 374,834 filed May 5, 1982, now abandoned.

The present invention is concerned with novel $N^2$-carboxymethyl-$N^6$-(substituted)lysyl and α-(ε-aminoalkyl)amino acid antihypertensive compounds which are effective inhibitors of angiotensin I converting enzyme. These novel compounds are, consequently, combined with pharmaceutically acceptable carriers to form pharmaceutical compositions of the present invention and are used in a method of treating hypertension.

Angiotensin II, a powerful vasoconstrictor hormonal peptide, is formed from the inactive angiotensin I by the action of angiotensin-converting enzyme. Recently, potent inhibitors of angiotensin-converting enzyme have been reported which are capable of lowering the blood pressure in hypertensive patients. The novel $N^2$-carboxymethyl-$N^6$-(substituted)lysyl-and α-(ε-aminoalkyl)glycyl amino acid antihypertensive compounds of the present invention are also potent inhibitors of angiotensin-converting enzyme.

2. Brief Description of the Prior Art

U.S. Pat. Nos. 4,113,715; 4,129,571; and 4,154,960 disclose substituted acyl derivatives of amino acids which are useful as angiotension converting enzyme inhibitors. More specifically, these compounds are mercapto substituted acyl amino acids and derivatives thereof including the clinically effective antihypertensive compound, captopril, i.e., D-3-mercapto-2-methylpropanoyl-L-proline.

The foregoing prior art compounds are not dipeptide derivatives as are the compounds of the present invention. Furthermore, these prior art compounds contain an essential sulfhydryl substituent or derivative thereof whereas those of the present invention do not. In addition, the dipeptide compounds of the present invention are unusual dipeptides whose N-terminus bears a carboxymethyl group which is preferably further substituted on the methyl group. In addition, the carboxyl group(s) may also be converted to ester, amide and salt derivatives. In effect, the compounds of the present invention are hybrids formed by fusing α-amino acids onto dipeptides by means of a nitrogen shared by these two part-structures. This structural arrangement is rare in the field of synthetic and natural peptides and is not suggested or disclosed by the mercaptoacyl type functions of the two prior art patents identified above.

U.S. Pat. No. 4,052,511 discloses N-carboxyalkanoylamino acids which are useful as angiotensin converting enzyme inhibitors. Since the compounds of the present invention are dipeptide derivatives, in a formal sense they may be considered to be related to some of the compounds disclosed in U.S. Pat. No. 4,052,511. However, when a particular one of the methylene groups is replaced by an amino function as in the present invention, compounds of surprisingly high potency are obtained. For example, the preferred compounds of the present invention can be administered in dosages as low as about 2.5 mg per patient per day as opposed to the lowest dosage level of 1 mg per kg per day for preferred compounds disclosed in the U.S. Pat. No. 4,052,511 which is about equivalent to 60 mg per patient per day based on an average patient weight of about 150 pounds.

DETAILED DESCRIPTION OF THE INVENTION AND PREFERRED EMBODIMENTS

In its broadest aspect, the present invention relates to novel $N^2$-carboxymethyl-$N^6$-(substituted)lysyl-and α-(ε-amino-alkyl)glycyl amino acid antihypertensive compounds of the formula:

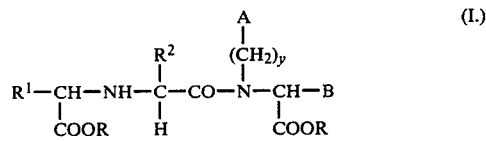

wherein:

R is hydrogen; loweralkyl; aralkyl; or aryl;

$R^1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di- or trisubstituted by loweralkyl, hydroxy, loweralkoxy, halo, amino, acylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n—Q—(CH_2)_m$ wherein n is 0–2, m is 1–3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, $N—R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl; in the group:

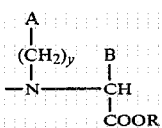

y is 0 to 4;

A is
- (a) alkyl, including branched unsaturated and cyclic alkyl of 3 to 8 carbon atoms;
- (b) benzofused cycloalkyl or bicycloalkyl of 8 to 12 carbon atoms;
- (c) aryl or heteroaryl groups which may be mono-, di- or trisubstituted by loweralkyl, loweralkoxy, halo, amino, acylamino, hydroxy, acyl or acyloxy, and corresponding groups in which the aryl or heteroaryl groups are partially or completely hydrogenated;
- (d) loweralkyl including branched and unsaturated groups which may be substituted by aryl or heteroaryl groups and corresponding groups in which the aryl or heteroaryl rings are partially or completely hydrogenated;

B is hydrogen or loweralkyl; or

A and B may be joined, together with the carbon atoms to which they are attached to form a ring having the formulae:

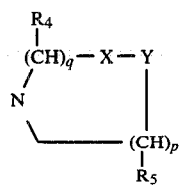

wherein X and Y taken together are

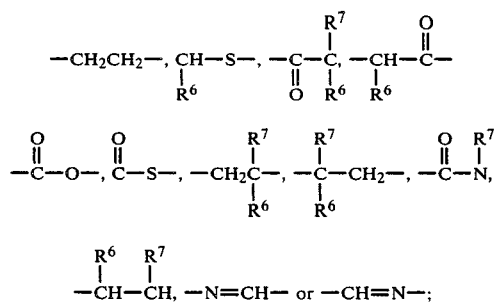

$R^5$ and $R^6$ individually are hydrogen; loweralkyl; cycloalkyl; aryl; aralkyl; heteroaryl; loweralkyloxy; loweralkylthio; aryloxy; arylthio; arloweralkyloxy; arloweralkylthio; hydroxy; acyloxy; acylloweralkyl; halo; amino; mono- or disubstituted loweralkylamino; arloweralkylamino; heteroloweralkylamino acylamino in which the acyl group may be loweralkanoyl, aroyl, heteroaroyl or heteroloweralkanoyl; carbamoyl or N-substituted carbamoyloxy; including any of these groups containing an aromatic ring wherein said ring may be mono-, di- or trisubstituted by loweralkyl, loweralkoxy, loweralkylthio, halo, hydroxy, aryl, aryloxy, arylthio or aralkyl; any of the groups recited above containing an aryl or heteroaryl group in which these groups are partially or completely hydrogenated;

$R^7$ is hydrogen, loweralkyl, cycloalkyl, aryl, substituted aryl wherein the substituent can be halo, hydroxy, alkoxy, amino, or loweralkyl; or $R^6$ and $R^7$ taken together may be oxo or together with the carbon atoms to which they are attached form a 3 to 6 membered ring which may contain 0, 1 or 2 atoms of N, S or O;

p and q are independently 0 to 3;

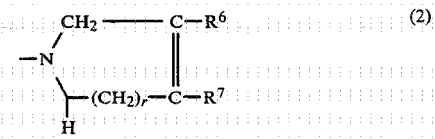

wherein $R^6$ and $R^7$ are as defined above and r is 0, 1 or 2;

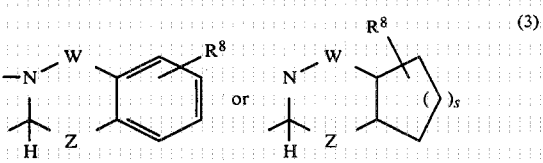

wherein: W is absent; —CH$_2$—;

$$-\overset{O}{\underset{\|}{C}}-;$$

N; or S; Z is —(CH$_2$)$_t$, wherein m is 0 to 2, provided that t may not be 0 when W is absent; —O—; —N—, or —S—;

$R^8$ is hydrogen; loweralkyl; loweralkoxy; hydroxy; halo; loweralkylthio; amino; acylamino; or cyano; s is 1 to 3;

$R^2$ is

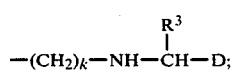

where k is 2 to 5; $R^3$ is hydrogen; loweralkyl and substituted lower-alkyl where the substituents are carboxy, hydroxy, and amino; or aralkyl, substituted aralkyl, heteroaralkyl, and substituted heteroaralkyl where the aryl and heteroaryl substituents are carboxy, hydroxy, and amino; and D is COOR; CONH$_2$; or CH$_2$OH;

and a pharmaceutically acceptable salt thereof.

The alkyl substituents recited above denote straight and branched chain hydrocarbons of $C_1$–$C_{12}$ such as methyl, hexyl, propyl, dodecyl isopentyl, isopropyl, nopentyl, etc.

Loweralkyl denotes alkyl groups of $C_1$ to $C_8$ such as ethyl, isobutyl, 4-methylpentyl, and the like.

Alkenyl and alkynyl denote alkyl groups as described above which are modified so that each contains a carbon to carbon double bond or triple bond, respectively, such as vinyl, 2-butenyl and 1-hexynyl.

Cycloalkyl denotes rings composed of 5 to 8 methylene groups, each which may be substituted or unsubstituted with other hydrocarbon substituents, and include, for example, cyclopentyl, cycloheptyl, 4-methyl cyclohexyl, and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:1:3 octane and spiro 4:0:4 nonane.

The loweralkoxy substituent represents a loweralkyl group as described above attached through an oxygen bridge.

The aralkyl and heteroaralkyl substituents recited above represent aryl or heteroaryl groups as herein above defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, for example, indolyl, quinolinyl, isoquinolinyl, benzimidazolyl, benzothiazolyl, benzthienyl, and naphthyridyl.

The acylamino substituent represents loweralkanoylamino and aroylamino.

Of the various heterocyclic elements generally defined above as $$\begin{array}{c} A \\ | \\ (CH_2)_y \\ | \\ -N-CH-B, \\ | \\ COOR \end{array}$$

the following are specifically included and are preferred:

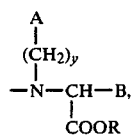

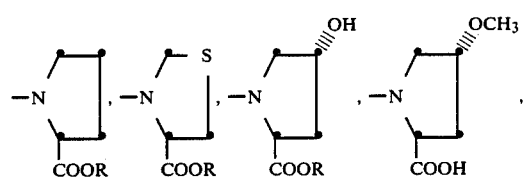

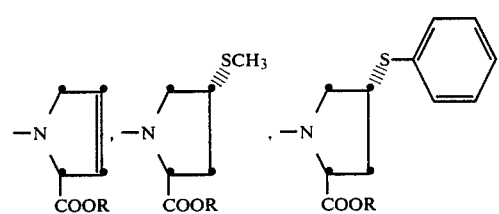

-continued

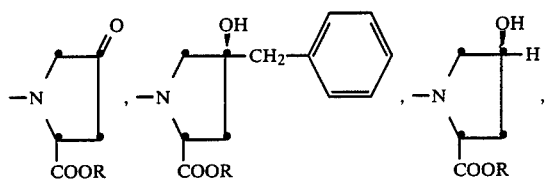

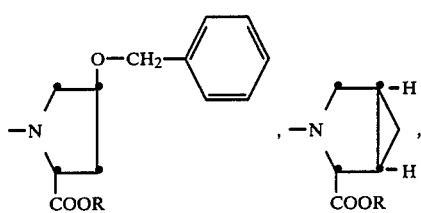

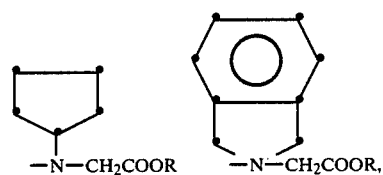

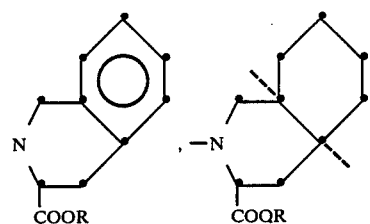

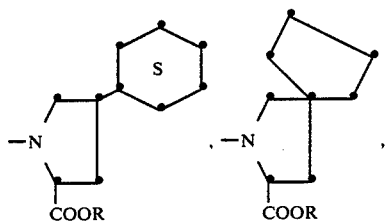

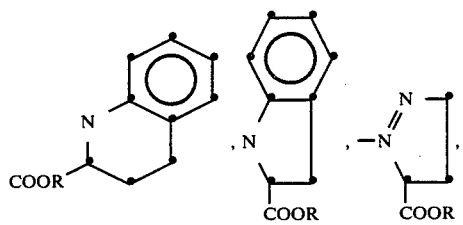

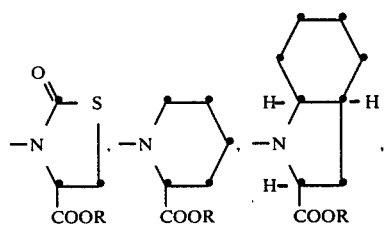

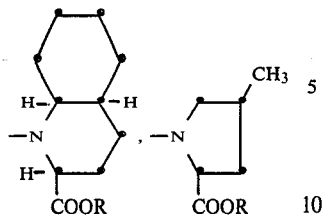

The Formula I compounds can be used in the form of salts derived from inorganic or organic acids and bases. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfoate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; alkali metal salts such as sodium and potassium salts, alkaline earth metal salts such as calcium and magnesium salts, ammonium salts; salts with organic bases such as dicyclohexylamine salts, N-methyl-D-glucamine; and salts with amino acids such as arginine and lysine. Water or oil-soluble or dispersible products are thereby obtained. The non-toxic physiologically acceptable salts are preferred although other salts are also useful, e.g., in isolating or purifying the desired product.

Preferred compounds of the present invention are those of Formula I wherein:

R is hydrogen or loweralkyl;

$R^1$ is alkyl of 1–10 carbon atoms which include branched, cyclic and unsaturated alkyl groups; substituted loweralkyl wherein the substituent can be hydroxy, lower alkylthio, amino, alkylamino, lowerdialkylamino, and acylamino; substituted loweralkyl having the formula $R_A{}^1(CH_2)_n—Q—(CH_2)_m—$ wherein n is 0–2, m is 1–3, $R_A{}^1$ is aryl or heteroaryl optionally substituted by alkyl, halo, dihalo, amino, cyano, hydroxy, or alkoxy, and Q is O, S, N—$R_B{}^1$, $CONR_C{}^1$, $NR_C{}^1CO$, or CH=CH wherein $R_B{}^1$ is hydrogen, loweralkyl, aralkyl, loweralkanoyl, or aroyl and $R_C{}^1$ is hydrogen or loweralkyl; aralkyl or heteroaralkyl which include branched loweralkyl groups; substituted aralkyl or substituted heteroaralkyl which include branched loweralkyl groups wherein the loweralkyl substituents can be amino, acylamino, or hydroxy and the aryl and heteroaryl substituents can be loweralkyl, halo, dihalo, amino, cyano, hydroxy, loweralkoxy, aminoloweralkyl, or hydroxyloweralkyl;

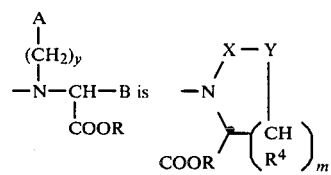

where X and Y taken together are —CH$_2$—CH$_2$—; $R^4$ is hydrogen; m is 1; and R is as previously defined;

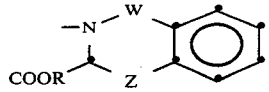

wherein W and Z are $CH_2$ and R is as defined above;

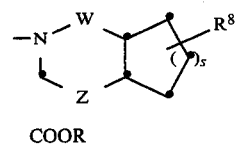

wherein W is O, Z is $CH_2$, $R^8$ is H, s is 2, and R is as defined above; and,

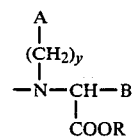

wherein y is O, A is 2-indanyl, B is H, and R is as defined above;

R is

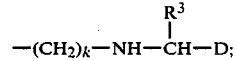

where k is 5; $R^3$ is hydrogen; loweralkyl and substituted loweralkyl where the substituents are carboxy, hydroxy, and amino; or aralkyl, substituted aralkyl, heteroaralkyl, and substituted heteroaralkyl where the aryl and heteroaryl substituents are carboxy, hydroxy, and amino; and D is COOR; $CONH_2$; or $CH_2OH$.

Especially preferred compounds of the present invention are the following:

N-[$N^2$-(1(S)-carboxy-3-phenylpropyl)-$N^6$-carboxymethyl-L-lysyl]-L-proline;

N-[$N^2$-(1(S)-carboxy-3-phenylpropyl)-$N^6$-carbamoylmethyl-L-lysyl]-L-proline;

N-[$N^2$-(1(S)-carboxy-3-phenylpropyl)-$N^6$-hydroxyethyl-L-lysyl]-L-proline;

N-[$N^2$-(1(S)-carboxy-3-phenylpropyl)-$N^6$-carboxymethyl-L-lysyl]-N-indanylglycine;

N-[$N^2$-(1(S)-carboxy-3-phenylptopyl)-$N^6$-carbamoylmethyl-L-lysyl]-N-indanylglycine;

N-[$N^2$-(1(S)-carboxy-3-phenylpropyl)-$N^6$-hydroxyethyl-L-lysyl]-N-indanylglycine;

N-[$N^2$-(1(S)-carboxy-3-phenylpropyl)-$N^6$-carboxymethyl-L-lysyl]-1,2,3,4-tetrahydroisoquinoline-3-carboxylic acid;

N-[$N^2$-(1(S)-carboxy-3-phenylpropyl)-$N^6$-carbamoylmethyl-L-lysyl]-1,2,3,4-tetrahydroisoquinoline-3-carboxylic;

N-[$N^2$-(1(S)-carboxy-3-phenylpropyl)-$N^6$-hydroxyethyl-L-lysyl]-1,2,3,4-tetrahydroisoquinoline-3-carboxylic acid;

N-[N²-(1(S)-carboxy-3-phenylpropyl)-N⁶-carboxymethyl-L-lysyl]-perhydroindole-2-carboxylic acid;

N-[N²-(1(S)-carboxy-3-phenylpropyl-N⁶-carbamoylmethyl-L-lysyl]-perhydroindole-2-carboxylic acid; and, N-[N²-(1(S)-carboxy-3-phenylpropyl)-N⁶-hydroxyethyl-L-lysyl]-perhydroindole-2-carboxylic acid.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodilator peptide, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanyl-histidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of the invention are useful in treating hypertension. They are also of value in the management of acute and chronic cohgestive heart failure, in the treatment of secondary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

Thus, in accordance with the present invention there is provided a pharmaceutical composition comprising a pharmaceutically acceptable carrier and a therapeutically effective amount of a compound of Formula I.

There is also provided, in accordance with the present invention, a method of treating hypertension comprising administering to a patient in need of such treatment a therapeutically effective amount of a compound of Formula I.

For the purpose of treating hypertension, and those clinical conditions noted above, the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl cellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hyroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacantn, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irritating excipient which is solid at ordinary temperatures by liquid at the rectal temperature and will thereofore melt in the rectum to release the drug. Such materials are cocoa butter and polyethylene glycols.

Dosage levels of the order of 1 to 200 mg per patient per day, in single or multiple doses, are useful in the treatment of the above indicated conditions. Preferably, the dosage range will be from 2.5 to 100 mg per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of this invention can also be administered in combination with other antihypertensives and/or diuretics. For example, the compounds of this invention can be given in combination with such compounds as acetazolamide, amiloride, aminophylline, atenolol, benzofluoromethiazide, benzthiazide, bumetanide, chlorthalidone, chlorothiazide, clonidine, cryptenamine acetates and cryptenamine tannates, cyclothiazide, deserpidine, diazoxide, diltiazem, (S)-1-[[2-(3,4-dimethoxyphenyl)ethyl]amino]-3-[[4-(2-thienyl)-1H-imidazol-2-yl]phenoxy]-2-propanol, ethacrynic acid, fluoromethiazide, furosemide, guanethidene sulfate, hydralazine hydrochloride, hydrochlorothiazaide, hydrofluoromethiazide, (+)-4-[3-[-[2-(1-hydroxycyclohexyl)ethyl]-4-oxo-2-thiazolidinyl]propyl]-benzoic acid, indacrinone and variable ratios of its enantiomers, merethoxylline procaine, methylclothiazide, methyldopa, methyldopate hydrochloride, metolazone, metoprolol tartate, minoxidil, naldolol, nifedipine, pargyline hydrochloride, pindolol, polythiazide, prazosin, propranolol, quinethazone, *rauwolfia serpentina*, rescinnamine, reserpine, sodium ethacrynate, sodium nitroprusside, spironolactone, ticrynafen, timolol, triamterene, trichlormethiazide, trimethophan camsylate, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective in the 2.5 to 100 mg per day range can be effectively combined at levels at the 0.5 to 100 mg per day range with the following compounds at the indicated per day dose range: hydrochlorothiazide (10–100 mg); chlorothiazide (125–2000 mg); manipulated indacrinone enantiomer ratio (25–150 mg); ethacrynic acid (15–2000 m 5–20 mg); furosemide (5–80 mg); propranolol (20–480 mg); timolol (5–60 mg); and methyldopa (65–2000 mg); and the pivaloyloxyethyl ester of methyldopa (30–1000 mg). In addition, triple drug combinations of hydrochlorothiazide (10–100 mg) plus amiloride (5–20 mg) plus converting enzyme inhibitor of this invention (0.5–100 mg); hydrochlorothiazide (10–100 mg) plus timolol (5–60 mg) plus the converting enzyme inhibitor of this invention (0.5–100 mg); or manipulated indacrinone enantiomer ratio (25–150 mg) plus amiloride (5–20 mg) plus converting enzyme inhibitor of this invention (0.5–100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of a compound or mixture of compounds of Formula I or a physiologicaly acceptable salt is compounded with a physiologically acceptable vehicle, carrier, excipient, binder, preservative, stablizer, flavor, etc., in a unit dosage form as called for by accepted pharmaceutical practice. The amount of active substance in these compositons or preparations is such that a suitable dosage in the range indicated is obtained.

The compounds of Formula I can be prepared by one or more of the methods described further below.

As will be evident to those skilled in the art and as demonstrated in the Examples which follow, reactive groups not involved in the reactions, such as amino, carboxy, mercapto, etc., may be protected by methods standard in peptide chemistry prior to the coupling reactions and subsequently deprotected to obtain the desired products.

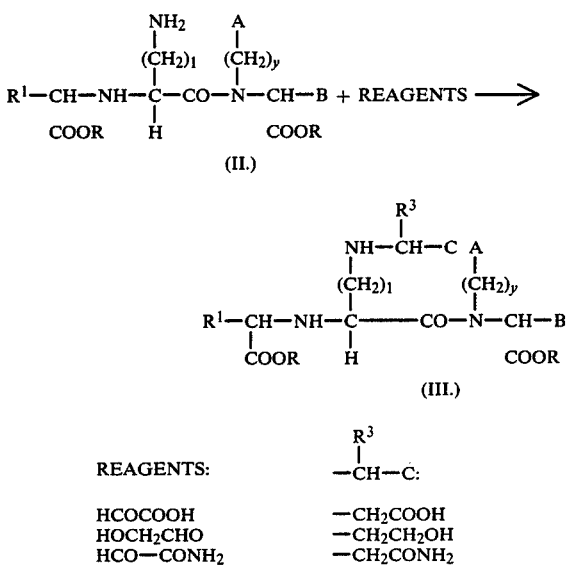

In the reactions illustrated above, the starting material of Formula I is condensed with the reagents described to form the desired product. The starting materials, which may be prepared in accordance with the procedures described in published European patent applicaton No. 0 012 401, are dissolved in a suitable solvent together with the desired reagent, and the mixture is subjected to hydrogenolysis using suitable means, preferably a Pd/carbon catalyst and Parr apparatus. A preferred starting material is: $N^2$-[1-(S)-carboxy-3-phenylpropyl[-L-lysyl-L-proline, which may be prepared in accordance with Example 57 of said European patent application No. 0 012 401.

The following examples serve to illustrate preparation of the novel compounds of the present invention, while not amounting to any limitation thereof.

EXAMPLE 1

N-[$N^2$-(1(S)-Carboxy-3-phenylpropyl)$N^6$-carboxmethyl-L-lysyl]-L-proline.

N-[$N^2$-(1(S)-carboxy-3-phenylpropyl)-L-lysyl]-L-proline (406 mg, 0.001 mole), glyoxylic acid hydrate (460 mg, 0.005 mole), and 10% Pd on carbon catalyst (200 mg) were mixed in methanol (5 ml) water (3.5 ml) and acetic acid (0.16 ml). The mixture was hydrogenolyzed on a Parr apparatus until the monoalkylation product was major by TLC, followed by filtrate through Supercel. The catalyst was washed with 1:1 methanol-water, and the filtrate was concentrated in vacuo. The residue was extracted twice with hot ethyl acetate. The crude product was then chromatographed on a 240×0.9 cm LH-20 column with methanol. Product rich fractions (cuts 27-31) were evaporated to dryness and freeze-dried to a white powdery solid (130 mg). Crystallization from methanol-ethyl acetate gave m.p. 150°-152° C.; the $R_f$ value (in Avicel) of this compound in iPrOH:NH$_4$OH: H$_2$O (7:1:2) was 0.49; MS (FAB): M+1 (464), and M+Na (486).

Anal. Calc'd for $C_{23}H_{33}N_3O_7$: C, 59.60; H, 7.18; N, 9.07. Found: C, 59.87; H, 7.12; N, 8.83.

EXAMPLE 2

N-[$N^2$-(1(S)-Carboxy-3-phenylpropyl)-$N^6$-hydroxyethyl-L-lysyl]-L-proline

The reductive alkylation of N-[$N^2$(1(S)-carboxy-3-phenylpropyl)-L-lysyl]-L-proline and glycoaldehyde was carried out in accordance with the procedures described above in Example 1.

The workup, including LH-20 chromatography, gave N-[$N^2$-(1(S)-carboxy-3-phenylpropyl)-$N^6$-hydroxyethyl-L-lysyl]-L-proline; yield: 76%; mass spectrum (FAB):M+1 (450).

EXAMPLE 3

Method A:

N-[$N^2$-(1(S)-Carboxy-3-phenylpropyl)-$N^6$-carbamoylmethyl-L-lysyl]-L-proline

In 4.0 ml of water there was dissolved N-[$N^2$-(1(S)-carboxy-3-phenylpropyl)-L-lysyl]-L-proline (406 mg, 0.0001 mole), after which triethylamine (364 mg, 0.0036 mole) was added, followed by slow, dropwise addition of a solution of 2-chloroacetamide (140.3 mg, 0.0015 mole) in 6.0 ml of ethanol. The reaction mixture was stirred at room temperature for 15 minutes, followed by refluxing with stirring for 15 hours. Thin layer chromatography indicated a nearly complete reaction, and the refluxing was continued for 2 more hours. The reaction mixture is allowed to cool and then concentrated under vacuum, flushed with benzene 3 times, then further concentrated under vacuum. The crude product was purified on a 2.5×240 cm LH-20 chromatographic column using a methanol system. Product-rich fractions were evaporated to dryness and freeze-dried to give N-[$N^2$-(1(S)-carboxy-3-phenylpropyl)-$N^6$-carbamoylmethyl-L-lysyl]-L-proline.

Method B

In the manner described above in Example 1, N-[$N^2$(1(S)-carboxy-3-phenylpropyl)-L-lysyl]-L-proline and glyoxylic acid amide (which can be prepared by the oxidation of glycolamide with pyridinum dichromate) were hydrogenated in the presence of 10% Pd on carbon catalyst to yield N-[$N^2$-(1(S)-carboxy-3-phenylpropyl)-$N^6$-carbamoylmethyl-L-lysyl]-L-proline.

Method C

The reductive alkylation of N-[$N^2$(1(S)-carboxy-3-phenylpropyl)-L-lysyl]-L-proline and ethyl glyoxylate was carried out in accordance with the procedures described in Example 1 to give N-[$N^2$-(1(S)-carboxy-3-phenylpropyl)-$N^6$-ethoxycarbonylmethyl-L-lysyl]-L-proline. The product was then treated with ammonia at 100° C. followed by absorption on strong acid ion exchange resin and eluting with 2% pyridine in water. Freeze drying of product-rich cuts afforded N-[$N^2$-(1(S)-carboxy-3-phenylpropyl)-$N^6$-carbamoylmethyl-L-lysyl]-L-proline. The nmr spectrum was consistent with the structure.

EXAMPLE 4

Additional products of Formula I can be prepared by employing the keto acids, carboxamides, and esters listed in Table I below. These are condensed with the desired intermediate in the presence of sodium cyanoborohydride, in accordance with the procedures described in the reaction scheme and Examples above. The N⁶-benzyloxycarbonyl group is then removed to give the desired product.

The desired intermediate will be of the formula:

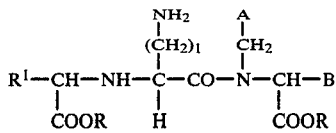

TABLE I

Keto Acids and Esters which can be used to prepare products of Formula I (a) C₆H₅—CH₂CH₂COCOOH (b) CH₃COCOOH (c) (CH₃)₂CHCH₂COCOOH (d) C₆H₅—(CH₂)₃COCOOC₂H₅

(e) Cl—C₆H₄—CH₂COCOOH (f) phthalimido—(CH₂)₄—COCOOH
(precursor for corresponding amino compound)

(g) thienyl—CH₂CH₂COCOOH (h) (CH₃)₂CHCOCOOC₂H₅

(i) (CH₃)₂CHCH₂CH₂COCOOH (j) HO—C₆H₄—CH₂CH₂COCOOH (k) (OH)C₆H₄—CH₂CH₂COCOOH (l) C₆H₅—CH₂COCONH₂

TABLE I-continued

Keto Acids and Esters which can be used to prepare products of Formula I (m) C₆H₅—CH₂COCOOCH₂C₆H₅

(n) C₆H₅—O—CH₂COCOOC₂H₅

(o) C₆H₅—S—CH₂COCONH₂

(p) naphthyl—CH₂CH₂COCOOH (q) CH₃S—CH₂CH₂COCOOH (r) C₆H₅—O—C₆H₄—CH₂CH₂COCOOCH₃

Additional examples of compounds of Formula I that can be synthesized by the processes described herein are illustrated by, but not limited to, the compounds shown in Table II below.

TABLE II

Additional Compounds of Formula I (A) [structure with naphthyl, CH₂CH₂, NH—CH₂CH₂OH, (CH₂)₄, indoline, HOOC, COOH]

(B) [structure with phenyl, (CH₂)₃, NH—CH₂COOH, (CH₂)₄, indoline, HOOC, COOH]

TABLE II-continued
Additional Compounds of Formula I (C) 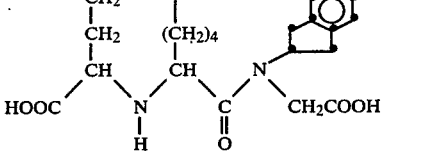

(D) 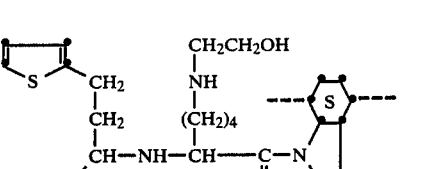

(E) 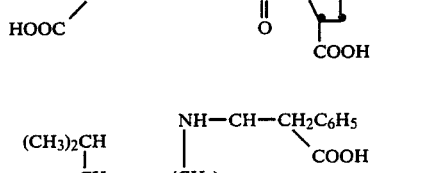

(F) 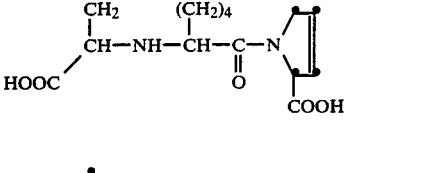

(G) 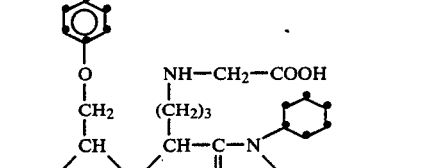

(H) 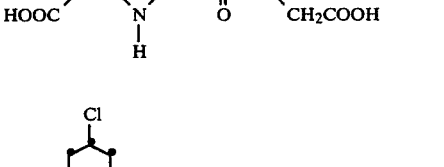

(I) 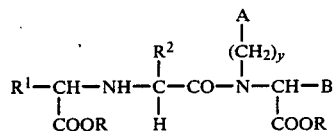

(J)

(K)

What is claimed is:
1. A compound of the formula:

$$R^1-CH-NH-\underset{\underset{H}{|}}{\overset{\overset{R^2}{|}}{C}}-CO-N-CH-B \quad (I.)$$
$$\overset{|}{COOR} \qquad \overset{|}{COOR}$$

with $A$ and $(CH_2)_y$ on the nitrogen.

wherein:
R is hydrogen; loweralkyl; aralkyl; or, aryl;
$R^1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino; substituted loweralkylamino, wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8-12 carbon atoms; aryl or heteroaryl which may be mono-, di- or trisubstituted by loweralkyl, hydroxy, loweralkoxy, halo, amino, acylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy; haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n\text{-}Q\text{-}(CH_2)_m$ wherein n is 0–2, m is 1–3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, SO$_2$, N—$R_B{}^1$, CONR$_C{}^1$, NR$_C{}^1$CO, CH=CH wherein $R_B{}^1$ is hydrogen, loweralkyl, aryl, aralkyl, loweralkanoyl, or aroyl, and $R_C{}^1$ is hydrogen, or loweralkyl; in the group:

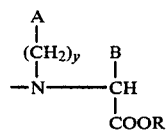

y is 0 to 4;

A is
(a) alkyl, including branched unsaturated and cyclic alkyl of 3 to 8 carbon atoms;
(b) benzofused cycloalkyl or bicycloalkyl of 8 to 12 carbon atoms;
(c) aryl or heteroaryl groups which may be mono-, di- or trisubstituted by loweralkyl; loweralkoxy, halo, amino, acylamino, hydroxy, acyl or acyloxy, and corresponding groups in which the aryl or heteroaryl groups are partially or completely hydrogenated;
(d) loweralkyl including branched and unsaturated groups which may be substituted by aryl or heteroaryl groups and corresponding groups in which the aryl or heteroaryl rings are partially or completely hydrogenated;

B is hydrogen or loweralkyl; or

A and B may be joined, together with the carbon atoms to which they are attached to form a ring having the formulae:

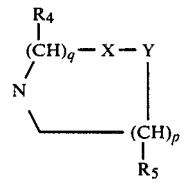

wherein X and Y taken together are

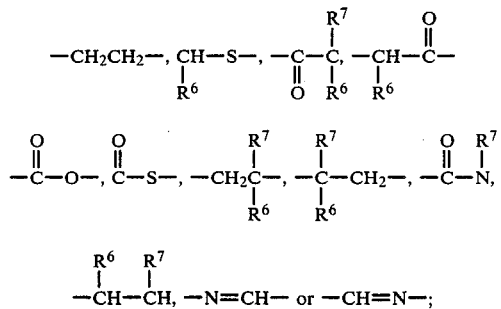

$R^5$ and $R^6$ individually are hydrogen; loweralkyl; cycloalkyl; aryl; aralkyl; heteroaryl; loweralkyloxy; loweralkylthio; aryloxy; arylthio; arloweralkyloxy; arloweralkylthio; hydroxy; acyloxy; acylloweralkyl; halo; amino; mono- or disubstituted loweralkylamino; arloweralkylamino; heteroloweralkylamino acylamino in which the acyl group may be loweralkanoyl, aroyl, heteroaroyl or heteroloweralkanoyl; carbamoyl or N-substituted carbamoyloxy; including any of these groups containing an aromatic ring wherein said ring may be mono-, di- or trisubstituted by loweralkyl, loweralkoxy, loweralkylthio, halo, hydroxy, aryl, aryloxy, arylthio or aralkyl; any of the groups recited above containing an aryl or heteroaryl group in which these groups are partially or completely hydrogenated;

$R^7$ is hydrogen, loweralkyl, cycloalkyl, aryl, substituted aryl wherein the substituent can be halo, hydroxy, alkoxy, amino or loweralkyl; or $R^6$ and $R^7$ taken together may be oxo or together with the carbon atoms to which they are attached form a 3 to 6 membered ring which may contain 0, 1 or 2 atoms of N, S or O;

p and q are independently 0 to 3;

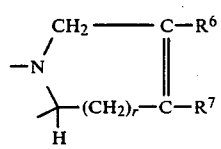

wherein $R^6$ and $R^7$ are as defined above and r is 0, 1 or 2;

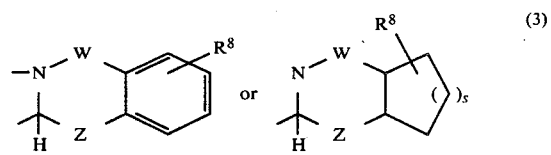

wherein:
W is absent; —CH$_2$—;

N; or S;
Z is —(CH$_2$)$_t$, wherein t is 0 to 2, provided that m may not be O when W is absent; —O—; —N—, or —S—.

$R^8$ is hydrogen; loweralkyl; loweralkoxy; hydroxy; halo; loweralkylthio; amino; acylamino; or cyano;
s is 1 to 3;
$R^2$ is

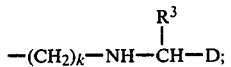

where k is 2 to 5; $R^3$ is hydrogen; loweralkyl and substituted loweralkyl where the substituents are carboxy, hydroxy, and amino; or aralkyl, substituted aralkyl, heteroaralkyl, and substituted heteroaralkyl where the aryl and heteroaryl substituents are carboxy, hydroxy, and amino; and D is $COOR$; $CONH_2$; or $CH_2OH$; and a pharmaceutically acceptable salt thereof.

2. A compound of claim 1 which is: N-[$N^2$-(1(S)-carboxy-3-phenylpropyl)-$N^6$-carboxymethyl-L-lysyl]-L-proline.

3. A compound of claim 1 which is: N-[$N^2$-(1(S)-carboxy-3-phenylpropyl)-$N^6$-carbamoylmethyl-L-lysyl]-L-proline.

4. A compound of claim 1 which is: N-[$N^2$-(1(S)-carboxy-3-phenylpropyl)-$N^6$-hydroxyethyl-L-lysyl]-L-proline.

5. A compound of claim 1 which is: N-[$N^2$-(1(S)-carboxy-3-phenylpropyl)-$N^6$carboxymethyl-L-lysyl]-N-indanylglycine.

6. A compound of claim 1 which is: N-[$N^2$-(1(S)-carboxy-3-phenylpropyl)-$N^6$-carbamoylmethyl-L-lysyl]-N-indanylglycine.

7. A compound of claim 1 which is: N-[$N^2$-(1(S)-carboxy-3-phenylpropyl)-$N^6$-hydroxyethyl-L-lysyl]-N-indanylglycine.

8. A compound of claim 1 which is: N-[$N^2$-(1(S)-carboxy-3-phenylpropyl)-$N^6$-carboxymethyl-L-lys 1]-1,2,3,4-tetrahydroisoquinoline-3-carboxylic acid.

9. A compound of claim 1 which is: N-[$N^2$-(1(S)carboxy-3-phenylpropyl)-$N^6$-carbamoylmethyl-L-lysyl]-1,2,3,4-tetrahydroisoquinoline-3-carboxylic acid.

10. A compound of claim 1 which is: N-[$N^2$-(1(S)-carboxy-3-phenylpropyl)-$N^6$-hydroxyethyl-L-lysyl]-1,2,3,4-tetrahydroisoquinoline-3-carboxylic acid.

11. A compound of claim 1 which is: N-[$N^2$-(1(S)-carboxy-3-phenylpropyl)-$N^6$-carboxymethyl-L-lysyl]-perhydroindole-2-carboxylic acid.

12. A compound of claim 1 which is: N-[$N^2$-(1(S)-carboxy-3-phenylpropyl)-$N^6$-carbamoylmethyl-L-lysyl]-perhydroindole-2-carboxylic acid.

13. A compound of claim 1 which is: N-[$N^2$-(1(S)-carboxy-3-phenylpropyl)-$N^6$-hydroxyethyl-L-lysyl]-perhydroindole-2-carboxylic acid.

14. A pharmaceutical composition useful in treating hypertension comprising a pharmaceutically acceptable carrier; and, an antihypertensively effective amount of a compound of claim 1.

15. A composition of claim 14 wherein said compound is a member selected from the group consisting essentially of:

N-[$N^2$-(1(S)-carboxy-3-phenylpropyl)-$N^6$-carboxymethyl-L-lysyl]-L-proline;

N-[$N^2$-(1(S)-carboxy-3-phenylpropyl)-$N^6$-carbamoylmethyl-L-lysyl]-L-proline;

N-[$N^2$-(1(S)-carboxy-3-phenylpropyl)-$N^6$-hydroxyethyl-L-lysyl]-L-proline;

N-[$N^2$-(2(S)-carboxy-3-phenylpropyl)-$N^6$-carboxymethyl-L-lysyl]-N-indanylglycine;

N-[$N^2$-(1(S)-carboxy-3-phenylptopyl)-$N^6$-carbamoylmethyl-L-lysyl]-N-indanylglycine;

N-[$N^2$-(1(S)-carboxy-3-phenylpropyl)-$N^6$-hydroxyethyl-L-lysyl]-N-indanylglycine;

N-[$N^2$-(1(S)-carboxy-3-phenylpropyl)-$N^6$-carboxymethyl-L-lysyl]-1,2,3,4-tetrahydroisoquinoline-3-carboxylic acid;

N-[$N^2$-(1(S)-carboxy-3-phenylptopyl)-$N^6$-carbamoylmethyl-L-lysyl]-1,2,3,4-tetrahydroisoquinoline-3-carboxylic;

N-[$N^2$-(1(S)-carboxy-3-phenylpropyl)-$N^6$-hydroxyethyl-L-lysyl]-1,2,3,4-tetrahydroisoquinoline-3-carboxylic acid;

N-[$N^2$-(1(S)-carboxy-3-phenylpropyl)-$N^6$-carboxymethyl-L-lysyl]-perhydroindole-2-carboxylic acid;

N-[$N^2$-(1(S)-carboxy-3-phenylpropyl)-$N^6$-carbamoylmethyl-L-lysyl]-perhydroindole-2-carboxylic acid; and, N-[$N^2$-(1(S)-carboxy-3-phenylpropyl)-$N^6$-hydroxyethyl-L-lysyl]-perhydroindole-2-carboxylic acid.

16. A method of treating hypertension comprising administering to a patient in need of such treatment an antihypertensively effective amount of a compound of claim 1.

17. The method of claim 16 wherein said compound is a member selected from the group consisting essentially of:

N-[$N^2$-(1(S)-carboxy-3-phenylpropyl)-$N^6$-carboxymethyl-L-lysyl]-L-proline;

N-[$N^2$-(1(S)-carboxy-3-phenylpropyl)-$N^6$-carbamoylmethyl-L-lysyl]-L-proline;

N-[$N^2$-(1(S)-carboxy-3-phenylpropyl)-N6-hydroxyethyl-L-lysyl]-L-proline;

N-[$N^2$-(2(S)-carboxy-3-phenylpropyl)-$N^6$-carboxymethyl-L-lysyl]-N-indanylglycine;

N-[$N^2$-(1(S)-carboxy-3-phenylpropyl)-$N^6$-carbamoylmethyl-L-lysyl]-N-indanylglycine;

N-[$N^2$-(1(S)-carboxy-3-phenylpropyl)-$N^6$-hydroxyethyl-L-lysyl]-N-indanylglycine;

N-[$N^2$-(1(S)-carboxy-3-phenylpropyl)-$N^6$-carboxymethyl-L-lysyl]-1,2,3,4-tetrahydroisoquinoline -3-carboxylic acid;

N-[$N^2$-(1(S)-carboxy-3-phenylpropyl-$N^6$-carbamoylmethyl-L-lysyl]-1,2,3,4-tetrahydroisoquinoline-b 3-carboxylic;

N-[$N^2$-(1(S)-carboxy-3-phenylpropyl)-$N^6$-hydroxyethyl-L-lysyl]-1,2,3,4-tetrahydroisoquinoline-3-carboxylic acid;

N-[$N^2$-(1(S)-carboxy-3-phenylpropyl)-$N^6$-hydroxyethyl-L-lysyl]-1,2,3,4-tetrahydroisoquinoline-3-carboxylic acid;

N-[$N^2$-(1(S)-carboxy-3-phenylpropyl-$N^6$-carbamoylmethyl-L-lysyl]-perhydroindole-2-carboxylic acid; and, N-[$N^2$-(1(S)-carboxy-3-phenylpropyl)-$N^6$-carbamoylmethyl-L-lysyl]-perhydroindole-2-carboxylic acid;

18. A pharmaceutical composition useful in the treatment of hypertension which comprises a pharmaceutically acceptable carrier; an antihypertensively effective amount of a compound of claim 1; and, an antihypertensive and/or diuretic compound selected from the group consisting of acetazolamide, amiloride, aminophylline, atenolol, behzofluoromethiazide, benzthiazide, bumetanide, chlorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)ethyl]amino]-3-[[4-(2-thienyl)-1H-imidazol-2-yl]phenoxy]-2-propanol, ethacrynic acid, fluoromethiazide, furosemide, guanethidene sulfate, hydralazine hydrochloride, hydrochlorothiazaide, hydrofluoromethiazide, (+)-4-[3-[-[2-(1-hydroxycyclohexyl)ethyl]-4-oxo-2-thiazolidinyl]propyl]-benzoic acid, indacrinone and variable ratios of its enantiomers, merethoxylline procaine, methylclothiazide, methyldopa, methyldopate hydrochloride, metolazone, metoprolol tartate, minoxidil, nadolol, nifedipine, pargyline hydrochloride, pindolol, polythiazide, prazosin, propranolol, quinethazone, *rauwolfia serpentina,* rescinnamine, reserpine, sodium ethacrynate, sodium nitroprusside, spironolactone, ticrynafen, timolol, triamterene, trichlormethiazide, trimethophan camsylate, verapamil.

19. The composition of claim 18 wherein said compound of claim 1 is a member selected from the group consisting essentially of:

N-[N$^2$-(1(S)-carboxy-3-phenylpropyl)-N$^6$-carboxymethyl-L-lysyl]-L-proline;

N-[N$^2$-(1(S)-carboxy-3-phenylpropyl)-N$^6$-carbamoylmethyl-L-lysyl]-L-proline;

N-[N$^2$-(1(S)-carboxy-3-phenylpropyl)-N$^6$-hydroxyethyl-L-lysyl]-L-proline;

N-[N$^2$-(2(S)-carboxy-3-phenylpropyl)-N$^6$-carboxymethyl-L-lysyl]-N-indanylglycine;

N-[N$^2$-(1(S)-carboxy-3-phenylpropyl)-N$^6$-carbamoylmethyl-L-lysyl]-N-indanylglycine;

N-[N$^2$-(1(S) carboxy-3-phenylpropyl)-N$^6$-hydroxyethyl-L-lysyl]-N-indanylglycine;

N-[N$^2$-(1(S)-carboxy-3-phenylpropyl)-N$^6$-carboxymethyl-L-lysyl]-1,2,3,4-tetrahydroisoquinoline-3-carboxylic acid;

N-[N$^2$-(1(S)-carboxy-3-phenylpropyl)-N$^6$-carbamoylmethyl-L-lysyl]-1,2,3,4-tetrahydroisoquinoline-3-carboxylic;

N-[N$^2$-(1(S)-carboxy-3-phenylpropyl)-N$^6$-hydroxyethyl-L-lysyl]-1,2,3,4-tetrahydroisoquinoline-3-carboxylic acid;

N-[N$^2$-(1(S)-carboxy-3-phenylpropyl)-N$^6$-carboxymethyl-L-lysyl]-perhydroindole-2-carboxylic acid;

N-[N$^2$-(1(S)-carboxy-3-phenylpropyl)-N$^6$-carbamoyl-methyl-L-lysyl]-perhydroindole-2-carboxylic acid;

methyl-L-lysyl]-perhydroindole-2-carboxylic acid; and,

N-[NW$^b$ $^2$-(1(S)-carboxy-3-phenylpropyl)-N$^6$-hydroxyethyl-L-lysyl]-perhydroindole-2-carboxylic acid.

20. A pharmaceutical composition useful in the treatment of hypertension which comprises a pharmaceutically acceptable carrier; an antihypertensively effective amount of a compound of claim 19; and a therapeutically effective amount of hydrochlorothiazide.

21. A pharmaceutical composition useful in the treatment of hypertension which comprises a pharmaceutically acceptable carrier; an antihypertensively effective amount of a compound of claim 19; and a therapeutically effective amount of timolol.

22. A pharmaceutical composition useful in the treatment of hypertension which comprises a pharmaceutically acceptable carrier; an anti-hypertensively effective amount of a compound of claim 19; and a therapeutically effective amount of manipulated indacrinone enantiomer ratio.

* * * * *